United States Patent [19]
Fletcher

[11] 4,302,586
[45] Nov. 24, 1981

[54] V-TRIAZOLYL-[4,5-D]-PYRIMIDINES
[75] Inventor: Ian J. Fletcher, Magden, Switzerland
[73] Assignee: Ciba-Geigy Corporation, Ardsley, N.Y.
[21] Appl. No.: 111,045
[22] Filed: Jan. 10, 1980
[30] Foreign Application Priority Data
Jan. 19, 1979 [CH] Switzerland ............................ 564/79
[51] Int. Cl.³ ...................... C07D 487/04; D06L 3/12
[52] U.S. Cl. ................................... 544/254; 544/118; 252/301.25
[58] Field of Search ................................ 544/254, 118

[56] References Cited
U.S. PATENT DOCUMENTS

| | | | |
|---|---|---|---|
| 2,543,333 | 2/1951 | Parker, et al. ...................... | 544/251 |
| 2,995,525 | 8/1961 | Crounse .......................... | 544/251 X |
| 3,817,990 | 6/1974 | Strobel et al. ...................... | 542/463 |
| 4,146,500 | 3/1979 | Fletcher et al. ................ | 252/301.21 |
| 4,157,443 | 6/1979 | Fletcher ............................ | 544/254 |

FOREIGN PATENT DOCUMENTS

| | | |
|---|---|---|
| 2554027 | 6/1976 | Fed. Rep. of Germany . |
| 2749902 | 5/1978 | Fed. Rep. of Germany . |
| 2099153 | 10/1972 | France . |

OTHER PUBLICATIONS
Review CIBA-GEIGY 1973/1, pp. 10-25.
Ganz, Applied Optics, 15, (9), pp. 2039-2058 (1976).
Ganz, Journal of Color and Appearance, 1, pp. 33-41 (1972).
Levene, et al., JSDC, Apr. 1978, pp. 144-149.
"Environmental Quality and Safety", Supplement vol. IV, Coulston, et al., eds., Academic Press, New York, (1975) pp. 83-94.
Prospectus for Spectrophotometer RFC3 of ZEISS.
Stensby, Soap & Chemical Specialties, Jul. 1967, pp. 80, 85-88.
Hartzel, et al., J. Am. Chem. Soc., vol. 76, pp. 2263-2265 (1954).
Timmis, et al., J. Pharmacy & Pharmacol., vol. 9, pp. 46-67 (1957).
Benson, et al., J. Am. Chem. Soc., vol. 72, pp. 1816-1818 (1950).

Primary Examiner—Donald G. Daus
Assistant Examiner—Diana G. Rivers
Attorney, Agent, or Firm—Edward McC. Roberts; John P. Spitals

[57] ABSTRACT
v-Triazolyl-[4,5-d]-pyrimidines of the formula

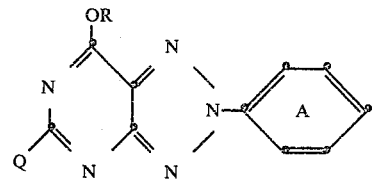

wherein Q is a mono- or disubstituted amino radical, R is an optionally substituted alkyl or aryl group and the benzene ring A can carry one or two substituents. The compounds are suitable as fluorescent whitening agents for organic material of high molecular weight, especially polyamide. The compounds are obtained by starting from a 4-aminopyrimidine which is correspondingly substituted in the 2- and 6-position, coupling it with the diazonium salt of an optionally substituted aniline and oxidising the resultant azo compound to the triazolyl-pyrimidine.

5 Claims, No Drawings

V-TRIAZOLYL-[4,5-D]-PYRIMIDINES

The present invention relates to novel v-triazolyl-[4,5-d]pyrimidines, processes for their manufacture and a method of optically whitening organic material of high molecular weight which comprises the use of these compounds.

v-triazolyl-[4,5-d]-pyrimidines, especially those which are substituted at the triazole ring by a phenyl radical, are known from the literature, in which connection reference is made to J. Am. Chem. Soc. 72 (1950), 1816–1818, J. Am. Chem. Soc. 76 (1954), 2263–2265, J. Pharmacy and Pharmacol. 9 (1957) 46–67, and U.S. patent specifications 2,543,333 and 2,995,525. A number of v-triazolyl-[4,5-d]-pyrimidines are also known as fluorescent whitening agents, in which connection attention is drawn to U.S. patent specification 3,817,990, German Offenlegungsschrift No. 2 749 902 and 2 554 027, and French patent specification 2 099 153.

Surprisingly, it has now been found that a selected group of v-triazolyl-[4,5-d]-pyrimidines which are substituted in a specific manner have especially advantageous whitening properties. The novel compounds also produce good white effects on polyester, which it has not proved possible to obtain with the compounds of the prior art cited above.

The novel v-triazolyl-[4,5-d]-pyrimidines have the formula

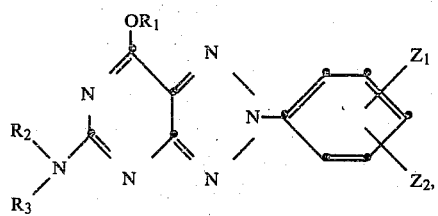

wherein $R_1$ is alkyl of 1 to 12 carbon atoms, alkoxyalkyl containing a total of 3 to 8 carbon atoms, alkenyl of 3 to 6 carbon atoms, phenyl which is unsubstituted or substituted by 1 to 3 members selected from the group consisting of halogen, alkyl or alkoxy, each of 1 to 4 carbon atoms, or is a group of the formula

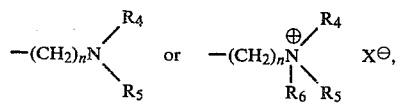

wherein each of $R_4$, $R_5$ and $R_6$ independently is alkyl of 1 to 4 carbon atoms, n is an integer from 2 to 6 and $X^\ominus$ is an anion; $R_2$ is alkyl of 1 to 12 carbon atoms, hydroxyalkyl of 2 to 6 carbon atoms or dialkylaminoalkyl containing 1 to 4 carbon atoms in each alkyl moiety; $R_3$ is hydrogen, alkyl of 1 to 12 carbon atoms or hydroxyalkyl of 2 to 6 carbon atoms, or $R_2$ and $R_3$ together with the nitrogen atom to which they are attached complete a 5- or 6- membered saturated heterocyclic ring which can additionally contain further heteroatoms as ring members; $Z_1$ is hydrogen, alkyl of 1 to 6 carbon atoms, alkoxy of 1 to 6 carbon atoms, alkenyloxy of 3 to 6 carbon atoms, hydroxyalkyl of 2 to 4 carbon atoms, alkoxyalkyl containing a total of 3 to 8 carbon atoms, benzyloxy, phenethoxy, halogen, phenoxy, phenoxyalkoxy containing 1 to 3 carbon atoms in the alkyl moiety, or is the group

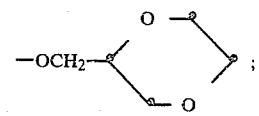

$Z_2$ is hydrogen, alkyl of 1 to 4 carbon atoms, alkoxy of 1 to 4 carbon atoms or halogen, or $Z_1$ and $Z_2$ in the ortho-position to each other are also the methylenedioxy, ethylenedioxy or methyleneoxymethyleneoxy radical.

Alkyl groups $R_1$, $R_2$ and $R_3$ contain preferably 1 to 6, most preferably 1 to 4, carbon atoms. A substituted phenyl group $R_1$ carries preferably 1 or 2, especially 1, of the groups specified above.

The term halogen indicates all halogen atoms, especially chlorine, fluorine and bromine, preferably chlorine.

The anion $X^\ominus$ is the anion of an inorganic or organic acid which is preferably introduced by quaternisation. Examples of such anions are halide, alkylsulfate and phenylsulfonate ions, or phenylsulfonate ions which are substituted by halogen and/or lower alkyl groups. Preferred anions are chloride, bromide, methylsulfate, ethylsulfate, phenylsulfonate, chlorophenylsulfonate and methylphenylsulfonate ions. Preferably one of the radicals $R_4$, $R_5$ and $R_6$ in a quaternised group $R_1$ is methyl and the anion $X^\ominus$ is the methylsulfate ion.

A further heteroatom which may be contained in a 5- or 6- membered saturated heterocyclic ring formed by $R_2$ and $R_3$ together with the nitrogen atom to which they are attached is preferably an oxygen or a nitrogen atom. Examples of such heterocyclic ring systems are pyrrolidine, piperidine, piperazine and morpholine, which can be unsubstituted or substituted by alkyl of 1 to 4 carbon atoms or halogen. Piperazine rings can be substituted in the 4-position by alkyl or hydroxyalkyl of 1 to 4 carbon atoms or also quaternised. Especially preferred heterocyclic ring systems are the unsubstituted pyrrolidine, piperidine or morpholine ring.

Within the scope of the formula I, important compounds are those of the formula

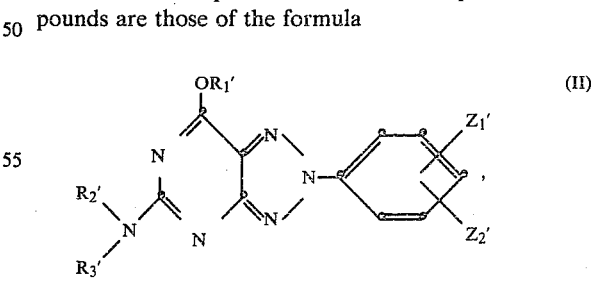

wherein $R_1'$ is alkyl of 1 to 6 carbon atoms, alkoxyalkyl containing a total of 3 to 8 carbon atoms, alkenyl of 3 or 4 carbon atoms, phenyl which is unsubstituted or substituted by one or two members selected from the group consisting of chlorine, fluorine, bromine, or alkyl or alkoxy, each of 1 to 4 carbon atoms, or is a group of the formula

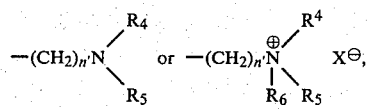

wherein each of $R_4$, $R_5$ and $R_6$ independently is alkyl of 1 to 4 carbon atoms, $n'$ is an integer from 2 to 4 and $X^\ominus$ is an anion; $R_2'$ is alkyl of 1 to 6 carbon atoms or hydroxyalkyl of 2 to 6 carbon atoms; $R_3'$ is hydrogen, alkyl of 1 to 6 carbon atoms or hydroxyalkyl of 2 to 6 carbon atoms, or $R_2'$ and $R_3'$ together with the nitrogen atom to which they are attached complete a 5- or 6-membered saturated heterocyclic ring which can additionally contain a further oxygen or nitrogen atom as ring member; $Z_1'$ is hydrogen, alkyl of 1 to 4 carbon atoms, alkoxy of 1 to 4 carbon atoms, allyloxy, hydroxyalkoxy of 2 to 4 carbon atoms, alkoxyalkoxy containing a total of 3 to 8 carbon atoms, benzyloxy, phenethoxy, chlorine, bromine, fluorine, phenoxy, phenoxypropoxy, or the group

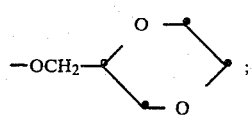

$Z_2'$ is hydrogen, alkyl of 1 to 4 carbon atoms, alkoxy of 1 to 4 carbon atoms, chlorine, bromine or fluorine, or $Z_1'$ and $Z_2'$ together in the ortho-position to each other are also the methylenedioxy, ethylenedioxy or methyleneoxymethyleneoxy radical.

Especially interesting compounds are v-triazolyl-[4,5-d]-pyrimidines of the formula

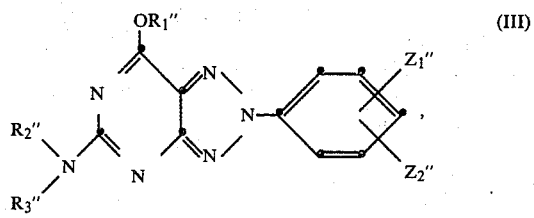

wherein $R_1''$ is alkyl of 1 to 4 carbon atoms, alkoxyalkyl containing a total of 3 to 6 carbon atoms, phenyl, chlorophenyl, methylphenyl, methoxyphenyl, or a group of the formula

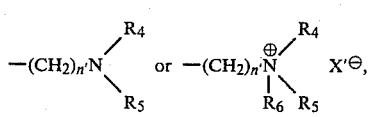

wherein $n'$ is an integer from 2 to 4, each of $R_4$, $R_5$ and $R_6$ independently is alkyl of 1 to 4 carbon atoms and $X'^\ominus$ is a halide or alkylsulfate ion or a phenylsulfonate ion which is unsubstituted or substituted by chlorine and/or methyl; $R_2''$ is alkyl of 1 to 4 carbon atoms, $R_3''$ is hydrogen or alkyl of 1 to 4 carbon atoms, or $R_2''$ and $R_3''$ together with the nitrogen atom to which they are attached form the pyrrolidine, piperidine or morpholine ring; $Z_1''$ is hydrogen, alkyl of 1 to 4 carbon atoms, alkoxy of 1 to 4 carbon atoms, allyloxy, hydroxyalkoxy of 2 to 4 carbon atoms, alkoxyalkoxy containing a total of 3 to 6 carbon atoms, benzyloxy, chlorine, or phenoxy; $Z_2''$ is hydrogen, alkyl of 1 to 4 carbon atoms, alkoxy of 1 to 4 carbon atoms or chlorine, or $Z_1''$ and $Z_2''$ together in the 3,4-position are the methylenedioxy, ethylenedioxy or methyleneoxymethyleneoxy radical.

Preferred compounds of the formula (III) are the v-triazolyl-[4,5-d]-pyrimidines of the formula

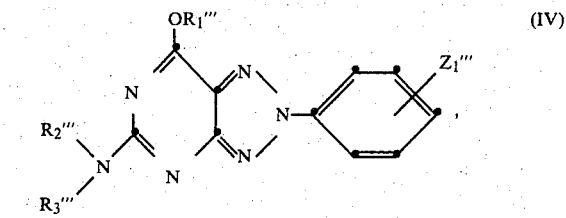

wherein $R_1'''$ is alkyl of 1 to 4 carbon atoms, alkoxyalkyl containing a total of 3 to 6 carbon atoms, phenyl or a group of the formula

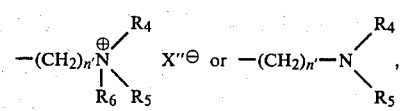

wherein $n'$ is an integer from 2 to 4, each of $R_4$, $R_5$ and $R_6$ independently is alkyl of 1 to 4 carbon atoms, and $R_6$ is preferably methyl, and $X''^\ominus$ is a chloride, bromide, iodide, methylsulfate, ethylsulfate or phenylsulfonate ion; $R_2'''$ is alkyl of 1 to 4 carbon atoms; $R_3'''$ is hydrogen or alkyl of 1 to 4 carbon atoms, or $R_2'''$ and $R_3'''$ together with the nitrogen atom to which they are attached form the morpholine or piperidine ring; and $Z_1'''$ is hydrogen, chlorine, alkyl of 1 to 4 carbon atoms, alkoxy of 1 to 4 carbon atoms, allyloxy, hydroxylalkoxy of 2 to 4 carbon atoms, alkoxyalkoxy containing a total of 3 to 6 carbon atoms, or a group of the formula

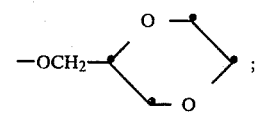

especially the v-triazolyl-[4,5-d]-pyrimidines of the formula

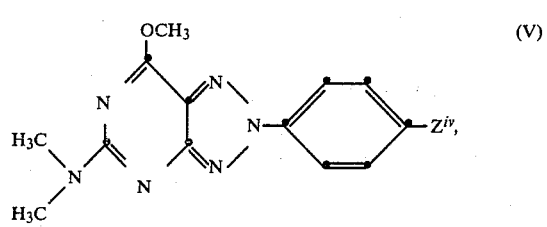

wherein $Z^{iv}$ is alkyl of 1 to 4 carbon atoms, alkoxy of 1 to 4 carbon atoms, hydroxyethyl or methoxyethyl.

The novel v-triazolyl-[4,5-d]-pyrimidines of the formula (I) can be obtained by methods which are known per se, for example by coupling an amine of the formula

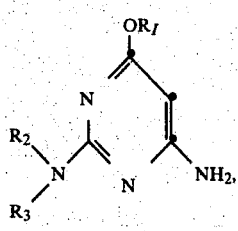 (VI)

wherein $R_1$, $R_2$ and $R_3$ have the given meanings, with a diazonium salt of the formula

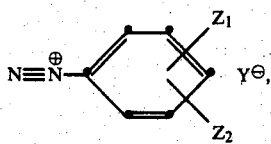 (VII)

wherein $Z_1$ and $Z_2$ are as defined above and $Y^\ominus$ is an anion, and oxidising the resultant azo compound of the formula

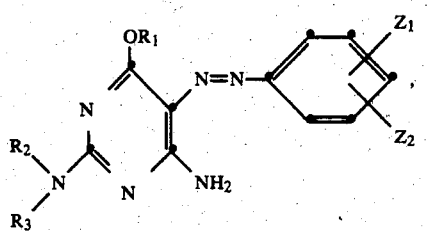 (VIII)

wherein $R_1$, $R_2$, $R_3$, $Z_1$ and $Z_2$ have the given meanings, to the triazolylpyrimidine of the formula (I).

A further process for obtaining compounds of the formula (I) consists in coupling an amine of the formula

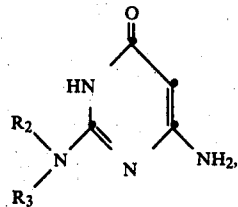 (IX)

wherein $R_2$ and $R_3$ have the given meanings, with a diazonium salt of the formula

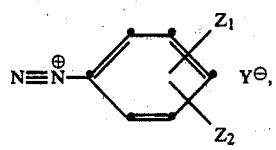 (VII)

wherein $Z_1$ and $Z_2$ are as defined above and $Y^\ominus$ is an anion, oxidising the resultant azo compound of the formula

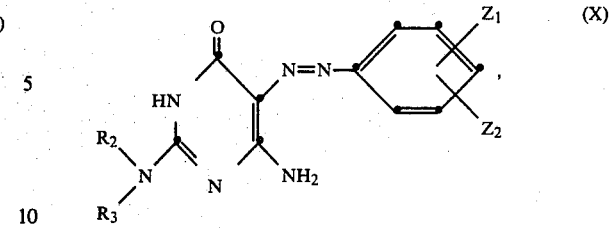 (X)

halogenating the triazolylpyrimidone thereby obtained, and reacting the resultant compound of the formula

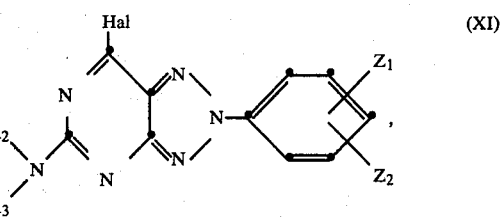 (XI)

wherein $R_2$, $R_3$, $Z_1$ and $Z_2$ have the given meanings and Hal is a halogen atom, with an alcoholate or phenolate of the formula $MOR_1$, in which $R_1$ has the given meaning and M is an alkali metal atom.

In the diazonium compound of the formula (VII), the anion Y is preferably a halogen ion, such as a chloride or bromide ion or a sulfate or tetrafluoroborate ion.

In both the processes described above the oxidation can be carried out by methods which are known per se, e.g. as described in U.S. patent specification No. 2,543,333. It is possible to use a wide range of oxidising agents, e.g. chromic acid, alkali bichromates, hydrogen peroxide, lead tetraacetate, potassium ferricyanide, ferric chloride, copper (II) sulfate. In an acid solvent, e.g. aqueous acetic acid, it is preferred to use an alkali bichromate, hydrogen peroxide or lead tetraacetate; and in a basic solvent, e.g. a pyridine/water mixture, potassium ferricyanide is preferably used. The oxidation is preferably carried out with copper (II) sulfate in a mixture of pyridine and water. The oxidation with a copper (II) salt, such as copper (II) sulfate or copper (II) chloride, is also advantageously carried out in methanol or a mixture of methanol and water in the presence of an ammonium or amine salt, such as a mono- or dialkanolamine. A compound of the formula (VII) is coupled with a compound of the formula (VI) or (IX) preferably in the temperature range between $-10°$ and $20°$ C. most preferably between $0°$ and $10°$ C. The oxidation is carried out in the temperature range between $70°$ and $100°$ C., preferably between $90°$ and $100°$ C.

The amino compounds of the formula (VI) employed as coupling components are known from the literature or they can be obtained by methods known from the literature. Reference is made in this connection to J. Amer. Chem. Soc, 73 (1951), 2864, J. Chem. Soc. 1962, 3172, Chem. Pharm. Bull. Japan 13 (1965), 557.

The aminopyrimidones of the formula (IX) employed as coupling components are either known or they can be obtained by methods which are known per se (cf. for example J. Amer. Chem. Soc. 73 (1951), 2864).

If the second reaction path described above is chosen, the halogenation of the azo compound of the formula (X) is effected by methods which are known per se (cf. for example J. Chem. Soc. 1968, 2076). Widely different halogenating agents can be employed. Preferably the compound of the formula (X) is chlorinated. This is accomplished by treating the latter e.g. with a phosphoroxy halide alone or in the presence of a tertiary organic base, for example in the presence of a N,N-dialkylaniline, a trialkylamine or of pyridine, or in the presence of a phosphorus pentahalide. This latter can also be employed alone as chlorinating agent. Suitable halogenating agents are also thionyl halides, preferably thionyl chloride, for example in dimethyl formamide as solvent.

The conversion of the halogenated compounds of the formula (XI) into compounds of the formula (I) is also carried out by methods which are known per se (cf. for example J. Org. Chem. 27 (1962), 4518). The procedure is that e.g. an alkali metal, for example sodium or potassium, especially sodium, is dissolved in an excess of the corresponding alcohol and a compound of the formula (XI) is treated with the resultant alcoholate of the formula $MOR_1$.

It is also possible to obtain the starting materials of the formula (VI) from the corresponding 2,4-diaminopyrimid-6-ones in the above described manner by halogenating the latter and reacting the resultant halogen compounds with a corresponding alcoholate of the formula $MOR_1$.

The diazonium salts of the formula (VII) can be obtained in conventional manner by diazotisation of the corresponding anilines. These anilines are known or they can be obtained by methods which are known per se, e.g. from chloronitrobenzenes by reaction with a suitable alcohol and subsequent reduction of the nitro group to the amino group.

The novel compounds defined above exhibit a more or less pronounced fluorescence in the dissolved or finely divided state. They can be used for optically whitening a wide variety of man-made, regenerated man-made or natural organic materials.

Without any restriction being implied by the following classification, examples of organic materials which can be treated with fluorescent whitening agents are:

I. Man-made organic materials of high molecular weight:

(a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds, for example acrylates, acrylic acid, acrylonitriles, acrylamides and their methacrylic analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, their homocondensation and co-condensation products, and aftertreatment products, for example polyesters, especially saturated polyesters (e.g. ethylene glycol terephthalic acid polyesters) or unsaturated polyesters (e.g. maleic acid-dialcohol polycondensates and their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and analogues, polycarbonates and silicones;

(d) polyadducts, such as polyurethanes (crosslinked and uncrosslinked) and epoxide resins.

II. Regenerated man-made organic materials, for example, cellulose esters of different degrees of esterification ($2\frac{1}{2}$-acetate or triacetate) or cellulose ethers, regenerated cellulose (viscose or cuprammonium cellulose), or their aftertreatment products, and casein plastics.

III. Natural organic materials of animal or vegetable origin, for example those based on cellulose or proteins, such as cotton, wool, linen, silk, natural film-forming resins, starch and casein.

The organic materials to be whitened can be in the most diverse states of processing (raw materials, semi-finished goods or finished goods). On the other hand, they can be in the form of structures of the most diverse shapes, for example predominantly three-dimensional structures such as sheets, profiles, injection mouldings, various machined articles, chips, granules or foams, and also predominantly two-dimensional structures, such as films, sheets, lacquers, coatings and impregnations or predominantly one dimensional bodies, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

Fibrous materials can be, for example, in the form of endless filaments (stretched or unstretched), staple fibres, flocks, hanks, textile filament yarns, threads, nonwovens, felts, waddings, flocked structures or woven textile or bonded textile fabrics, knitted fabrics, and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be whitened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of whitening agent used, it can be advantageous to carry out the treatment in a neutral or alkaline or acid bath. The treatment is usually carried out in the temperature-range from 20° to 140° C., for example at the boiling point of the bath or near it (about 90° C.).

For providing textile substrates with a finish in accordance with this invention it is also possible to employ solutions or emulsions in organic solvents, as is practised in the dyeing industry in so-called solvent dyeing (pad-thermofixation application, or exhaust dyeing methods in dyeing machines).

The fluorescent whitening agents of the present invention can further be added to, or incorporated in, the materials before or during their shaping. Thus they can for example be added to the compression moulding composition or injection moulding composition during the manufacture of films, sheets (for example incorporated in polyvinyl chloride in a roller mill at elevated temperature) or mouldings.

If man-made synthetic or regenerated man-made organic materials are formed by spinning processes or from spinning solutions/melts, the fluorescent whitening agents can be applied by the following processes:

addition to the starting materials (for example monomers) or intermediates (for example precondensates or prepolymers), that is to say before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

The fluorescent whitening agents of the present invention can, for example, also be employed in the following formulations:

(a) in mixtures with dyestuffs (shading) or pigments (coloured pigments or especially, for example, white pigments), or as an additive to dyebaths, printing pastes, discharge pastes or reserve pastes, or for the aftertreatment of dyeings, prints or discharge prints;

(b) in mixtures with carriers, wetting agents, plasticisers, swelling agents, antioxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft handle finishes, antisoiling finishes or antistatic finishes, or antimicrobial finishes;

(d) incorporation of the fluorescent whitening agents in polymer carriers (polymerisation, polycondensation or polyaddition products, in a dissolved or dispersed form, for use, for example, in coating agents, impregnating agents or binders (solutions, dispersions and emulsions) for textiles, nonwovens, papers and leather;

(e) as additives to master batches;

(f) as additives to a wide variety of industrial products in order to render these more marketable (for example improving the appearance of soaps, detergents, pigments);

(g) in combination with other substances with fluorescent whitening properties;

(h) in spinning bath preparations, that is to say as additives to spinning baths which are used for improving the slip for the further processing of synthetic fibres, or from a special bath before the stretching of the fibre.

If the whitening method is combined with textile treatment or finishing methods, the combined treatment can in many cases advantageously be carried out with the aid of appropriate stable preparations which contain the fluorescent whitener compounds in a concentration such that the desired white effect is achieved.

In certain cases, the fluorescent whitening agents are made fully effective by an aftertreatment. This can be, for example, a chemical treatment (for example acid treatment), a thermal treatment or a combined chemical/thermal treatment. Thus, for example, the appropriate procedure to follow in whitening a number of fibre substrates, for example polyester fibres, with the fluorescent whitening agents of the present invention, is to impregnate these fibres with the aqueous dispersions (or optionally also solutions) of the whitening agents at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or be combined in a single process stage.

The amount of fluorescent whitening agent of the present invention to be used, based on the weight of the material to be whitened, can vary within wide limits. A marked and lasting effect can be obtained even with very insignificant amounts, in certain cases 0.0001 percent by weight. But it is also possible to use amounts of up to 0.8 percent by weight and on occasion, up to 2 percent by weight. For most practical purposes, it is preferable to use amounts between 0.01 and 0.5 percent by weight.

For various reasons it is often advantageous not to use the fluorescent whitening agents by themselves, i.e. pure, but in admixture with a wide variety of assistants and extenders, for example anhydrous sodium sulfate, sodium sulfate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The fluorescent whitening agents of this invention are also particularly suitable for use as additives to wash liquors or heavy duty and domestic detergents, to which they can be added in various ways. They are appropriately added to wash liquors in the form of their solutions in water or organic solvents, or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistants, as a dry brightening powder. For example, the brightening agents can be mixed, kneaded or ground with the active detergents and, in this form, admixed with the finishing powder. However, they can be sprayed in a dissolved or pre-dispersed form on the finished detergent.

Suitable detergents are the known mixtures of active detergents, for example soap in the form of chips and powders, synthetics, soluble salts of sulfonic acid hemiesters of higher fatty alcohols, arylsulfonic acids with higher and/or multiple alkyl substituents, sulfocarboxylic acid esters of medium to high alcohols, fatty acid acylaminoalkyl- or acylaminoaryl-glycerol sulfonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminetetraacetic acid, and foam stabilisers, such as alkanolamides of higher fatty acids. The detergents can further contain for example: antistatic agents, fat restorative skin protectives, such as lanolin, enzymes, antimicrobial agents, perfumes and colourants.

The novel fluorescent whitening agents have the particular advantage that they are also active in the presence of active chlorine donors, for example, hypochlorite, and can be used without significant loss of effect in wash liquors containing nonionic tensides, for example alkylphenol polyglycol ethers.

The compounds of the invention are added in amounts of 0.005 to 1% or more, based on the weight of the liquid or pulverulent finished detergent. Wash liquors which contain the indicated amounts of the claimed fluorescent whiteners impart a brilliant appearance in daylight when used to wash textiles made from cellulose fibres, polyamide fibres, cellulose fibres with a high quality finish, polyester fibres or wool.

The washing treatment is carried out as follows, for example:

The textiles are treated for 1 to 30 minutes at 20° to 100° C. in a wash liquor which contains 1 to 10 g/kg of a built-up composite detergent and 0.05 go 1%, based on the weight of the detergent, of the claimed whitening agents. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching additive.

In the following Examples, parts and percentages are always by weight, unless otherwise stated. Unless indicated to the contrary, melting points and boiling points are uncorrected.

EXAMPLE 1:

3.7 g of p-anisidine are stirred in 15 ml of water and 7.5 g of concentrated hydrochloric acid. The mixture is cooled to 0° to 5° C. and diazotised at this temperature with a solution of 2.1 g of sodium nitrite in 5 ml of water. The diazo solution is stirred for a further 30 minutes at 0° to 5° C., then added dropwise at this temperature to a solution (cooled beforehand to 0° C.) of 5.05 g of 4-amino-2-dimethylamino-6-methoxypyrimidine in 20 ml of pyridine, such that the temperature does not exceed 10° C. When the addition is complete, the suspension thus obtained is stirred for 4 hours without cooling and then cooled to 5° C. The solid obtained is collected by suction, washed with water ans dried in vacuo at 80° C., affording 8.6 g (95% of theory) of the yellow azo compound of the formula

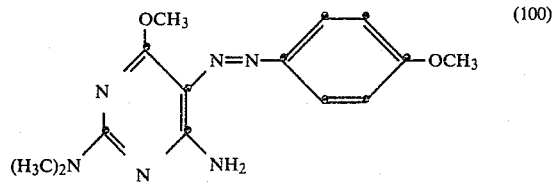

with a melting point of 188°–193° C.

With stirring, 8.6 g of the above azo compound are dissolved in 80 ml of pyridine at 70° C. and to this solution is added at 65°–70° C. a solution of 17.7 g of copper (II) sulfate pentahydrate in 80 ml of water. The mixture is subsequently stirred for 6 hours under reflux, cooled to 0° C. and filtered with suction. The crude product is washed with water and dried in vacuo at 80° C. Recrystallisation from toluene with the addition of fuller's earth yields 6.5 g (76% of theory) of the compound of the formula

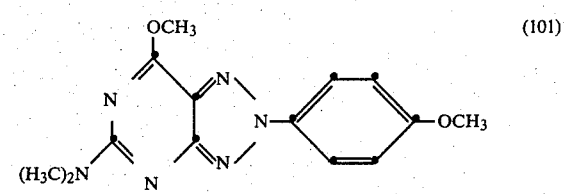

in the form of faintly yellow crystals with a melting point of 206.5°–208° C.

The compounds of the formula

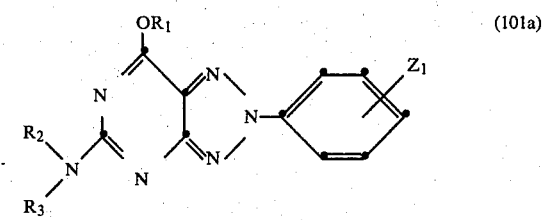

listed in Table 1 are obtained by the above described procedure using the corresponding 4-amino-2-dialkylamino-6-oxypyrimidines and optionally substituted anilines as starting materials.

TABLE 1

| No. | $R_2$ | $R_3$ | $R_1$ | $Z_1$ | Melting point in °C. |
|---|---|---|---|---|---|
| 102 | $CH_3$ | $CH_3$ | $CH_3$ | 4-$CH_3$ | 205.5–206.5 |
| 103 | $CH_3$ | $CH_3$ | $CH_3$ | H | 196–197 |
| 104 | $CH_3$ | $CH_3$ | $CH_3$ | 4-Cl | 241–244 |
| 105 | $CH_3$ | $CH_3$ | $CH_3$ | 3-Cl | 194–195 |
| 106 | $CH_3$ | $CH_3$ | $CH_3$ | 3-$CH_3$ | 144–145 |
| 107 | $CH_3$ | $CH_3$ | $CH_3$ | 3-$CH_2CH_3$ | 131–132 |
| 108 | $CH_3$ | $CH_3$ | $CH_3$ | 4-$CH_2CH_3$ | 206–207 |
| 109 | $CH_3$ | $CH_3$ | $CH_3$ | 3-$OCH_3$ | 182.5–183.5 |
| 110 | $CH_3$ | $CH_3$ | $CH_3$ | 4-$OCH_2CH_3$ | 209–210 |
| 111 | $CH_3$ | $CH_3$ | $CH_3$ | 4-$CH_2CH_2CH_2CH_3$ | 134–135 |
| 112 | $CH_3$ | $CH_3$ | $CH_3$ | 4-$OCH_2CH=CH_2$ | 173–174 |
| 113 | $CH_3$ | $CH_3$ | $CH_3$ | 4-$OCH_2CH_2OH$ | 218–219 |
| 114 | $CH_3$ | $CH_3$ | $CH_3$ | 4-$OC(CH_3)_3$ | 145–146 |
| 115 | $CH_3$ | $CH_3$ | $CH_3$ | 4-$OCH_2CH_2OCH_3$ | 179–180 |
| 116 | (morpholino) | | $CH_3$ | H | 163–165 |
| 117 | (morpholino) | | $CH_3$ | 4-$CH_3$ | 214–216 |
| 118 | (morpholino) | | $CH_3$ | 4-$OCH_3$ | 188–191 |
| 119 | $CH_3$ | $CH_3$ | $CH_2CH_3$ | 4-$CH_3$ | 224–225 |
| 120 | $CH_3$ | $CH_3$ | $CH_2CH_2OCH_3$ | 4-$CH_3$ | 175–176 |
| 121 | $CH_3$ | $CH_3$ | $CH_2CH_3$ | 4-$OCH_3$ | 174–176 |

TABLE 1-continued

| No. | R₂ | R₃ | R₁ | Z₁ | Melting point in °C. |
|-----|----|----|----|----|----------------------|
| 122 | CH₃ | CH₃ | CH₂CH₂<br>\|<br>OCH₃ | 4-OCH₃ | 166–167 |
| 123 | CH₃ | CH₃ | C₆H₅ | H | 182.5–183.5 |
| 124 | CH₃ | CH₃ | C₆H₅ | 4-OCH₃ | 202.5–204.5 |

The 4-amino-6-methoxy-2-morpholinopyrimidine requires as starting material for obtaining compounds (116) to (118) is prepared as follows:

60.46 g of 4-amino-6-chloro-2-morpholinopyrimidine (described in Chem. Pharm. Bull. 13, 557) are suspended in 190 ml of 1,2-dimethoxyethane and to this suspension are added 35.4 g of sodium methylate. The suspension is subsequently stirred for 22 hours under reflux and then cooled to 20° C. After addition of 180 ml of water the precipitated product is collected by suction and dried in vacuo at 80° C., affording 39.1 g (66% of theory) of 4-amino-6-methoxy-2-morpholinopyrimidine with a melting point of 162° C.–164° C.

The 4-amino-2-dimethylamino-6-(2-methoxyethoxy)-pyrimidine required for obtaining the compounds (120) and (122) is prepared as follows:

With efficient stirring, 3.22 g of sodium are dissolved at 20° C. in 200 ml of methyl cellosolve. To this solution are added 24.0 g of 4-amino-6-chloro-2-dimethylaminopyrimidine (known from J. Chem. Soc. 1952, 1532). The mixture is subsequently stirred for 36 hours under reflux and then cooled to 20° C. The precipitated sodium chloride is collected by suction and the mother liquor is concentrated to dryness. The desired product is obtained in quantitative yield and has a melting point of 78°–80° C.

The 4-amino-2-dimethylamino-6-phenoxypyrimidine required for obtaining compounds (123) and (124) is prepared as follows: With efficient stirring, 10.0 g of 4-amino-6-chloro-2-dimethylaminopyrimidine and 12.0 g of potassium carbonate are heated in 80.0 g of phenol to 150°–160° C. The clear melt is stirred overnight at this temperature and then poured into 3000 ml of a 5% potassium hydroxide solution. The precipitate is collected by suction, washed neutral with water and dried in vacuo, affording 12.3 g (92% of theory) of the desired product which melts at 110°–111° C.

EXAMPLE 2

15.7 g of (p-aminophenoxy)methyl-1,4-dioxane are dissolved in 19.0 g of concentrated hydrochloric acid and 40 ml of water. The solution is cooled to 0° C. to 5° C. and diazotised at this temperature with a solution of 5.3 g of sodium nitrite in 12 ml of water as in Example 1. 15.4 g of 6-amino-2-dimethylaminopyrimid-4-one are suspended in 50 ml of pyridine and the suspension is cooled to 0° C. To the suspension is added at 0° to 10° C. the solution of the diazonium salt. The batch is stirred for 3 hours at 0° to 5° C., then for 18 hours at 20° C. The orange-coloured azo compound of the formula

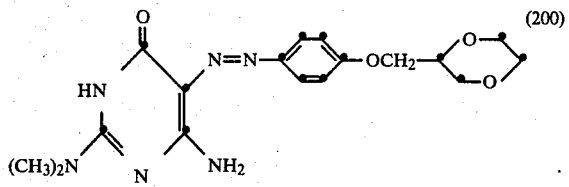

is collected by suction and dried in vacuo at 70° C.

The above azo compound is then suspended in 300 ml of pyridine at 60° C. and, at this temperature, a solution of 46.8 g of copper (II) sulfate pentahydrate in 300 ml of water is added to the suspension. The batch is then stirred for 18 hours at 90° to 100° C. The pyridine is then removed from the dark suspension by steam distillation. After cooling, the solid is filtered off with suction, washed with dilute hydrochloric acid and with water, and dried in vacuo at 70° C., affording 22.8 g (81% of theory) of the triazole pyrimidone of the formula

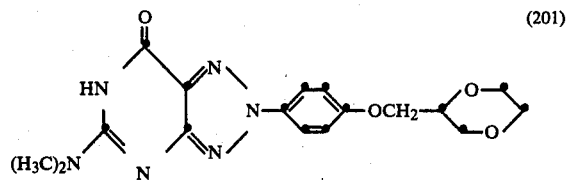

22.8 g of this compound are slowly heated to reflux temperature in 200 ml of phosphoroxy chloride and then stirred for 4 hours. Excess phosphoroxy chloride is then distilled off in vacuo and the residue is poured into water and adjusted to pH 4 with concentrated ammonia.

The precipitated yellowish green crystals are collected by suction, washed with water and dried in vacuo at 70° C. Recrystallisation from toluene yields 14.6 g (61% of theory) of the compound of the formula

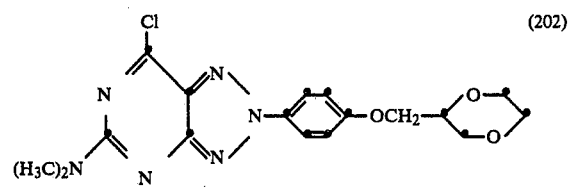

with a melting point of 178°–179° C.

7.2 g of this compound and 2.1 g of sodium methylate are stirred in 200 ml of 1,2-dimethoxyethane for 22 hours under reflux. The mixture is cooled to room temperature and then concentrated. Water is added to the residue and the precipitated product is collected by suction, washed with water and dried in vacuo. The crude product is recrystallised twice from ligroin with the addition of fuller's earth, affording 1.9 g (27% of theory) of the compound of the formula stituted 6-amino-2-dialkylaminopyrimid-4-ones, anilines and sodium alcoholates as starting materials.

| No. | R₂ | R₃ | R₁ | Z₁ | Melting point in °C. |
|---|---|---|---|---|---|
| 205 | —CH₂CH₃ | —CH₂CH₃ | CH₃ | OCH₃ | 131–133 |
| 206 | —CH₂CH₃ | —CH₂CH₃ | —CH(CH₃)₂ | CH₃ | 128–129 |
| 207 | CH₃ | CH₃ | —(CH₂)₃N(CH₃)₂ | OCH₃ | 116–118 |
| 208 | 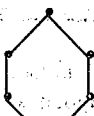 | | CH₃ | H | 171.5–173 |
| 209 | 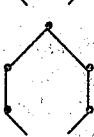 | | CH₃ | OCH₃ | 188–189.5 |

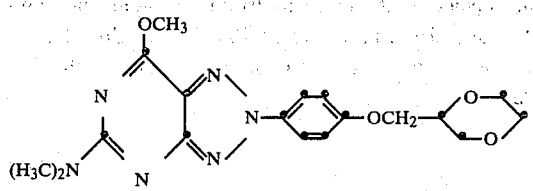

with a melting point of 180°–182° C.

The starting (p-aminophenoxy)-methyl-1,4-dioxane is prepared as follows:

46.2 g of iron filings, 46 ml of water and 9 ml of glacial acetic acid are stirred for 30 minutes at 95° C. Then 150 ml of cyclohexanone are added and, when the temperature has again risen to 95° C., 36.8 g of (p-nitrophenoxy)methyl-1,4-dioxane (known from British patent specification 749 713) are added in portions. The batch is then stirred for 3½ hours at 95° C. and, after addition of 9.0 g of sodium carbonate in portions, filtered hot. The residue is washed with cyclohexanone and the filtrate is subjected to steam distillation. After cooling, the product precipitates in the form of white crystals which are separated from a dark oil and recrystallised from water with the addition of animal charcoal. The crystals are dried in vacuo at 60° C., affording 16.3 g (51% of theory) of (p-aminophenoxy)methyl-1,4-dioxane of the formula

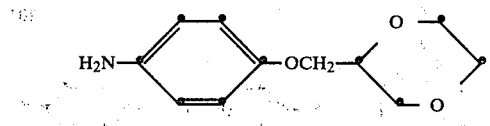

with a melting point of 86°–87° C.

The compounds of the formula

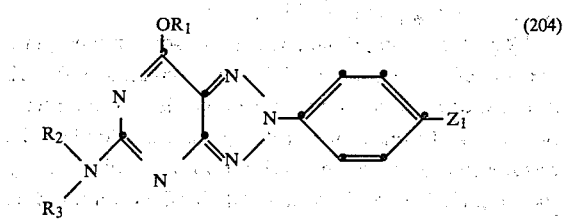  (204)

listed in Table 2 are obtained by the procedure described above using the corresponding optionally sub- The 6-amino-2-diethylamino-pyrimid-4-one required for obtaining compounds (205) and (206) is prepared as follows:

31.0 g of 1,1-diethylguanidine hydrochloride are dissolved in 70 ml of methanol and to this solution is added a solution of 11.6 g of sodium methylate in 70 ml of methanol. The mixture is then heated to reflux temperature and 20.2 g of methyl cyanoacetate are added dropwise. The reaction mixture is then stirred for 23 hours under reflux, cooled to 20° C., and the solution is adjusted to pH 7 with concentrated hydrochloric acid and concentrated. The residue is recrystallized twice from isopropanol/water with the addition of animal charcoal, affording 26.5 g (71% of theory) of the desired pyrimidone with a melting point of 144°–147° C.

The 6-amino-2-piperidino-pyrimid-4-one (m.p. 205° C.) required as starting material for obtaining compounds (208) and (209) is prepared in analogous manner starting from 1-piperidino-carboxamidine sulfate.

EXAMPLE 3

1.9 g of the compound (207) are dissolved in 50 ml of toluene at 30° C., then 0.76 g of dimethyl sulfate is added and the mixture is stirred for 18 hours under reflux to form a dense slurry. After cooling to 20° C., the precipitate is collected by suction and washed with toluene. The moist filter cake is recrystallised from ethanol with the addition of animal charcoal and dried in vacuo at 70° C., affording 2.0 g (80% of theory) of the compound of the formula

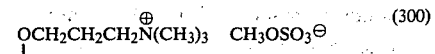

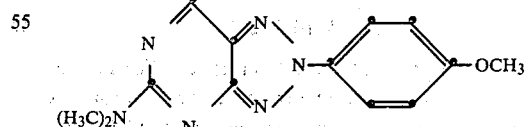  (300)

with a melting point of 223°–224° C.

EXAMPLE 4

5 g of polyester staple fibre fabric are put at 40° C. into 100 ml of an aqueous bath which contains 0.01 g of the fluorescent whitening agent of the formula (102) and 0.1 g of a fatty alcohol polyglycol ether. The bath is then heated in the course of 30 minutes to 120° C., kept for 30 minutes at this temperature, and then cooled in the course of 15 minutes to 40° C. The above treatment is carried out in a conventional dyeing machine. The fabric is given an aftertreatment by rinsing it for 30 seconds in running deionised water, then dried at 180° to 190° C. The treated fabric has a strong white effect.

EXAMPLE 5

5 g of cellulose acetate fabric is put at 40° C. into 100 ml of an aqueous bath which contains 0.005 g of the fluorescent whitening agent of the formula (101), 0.1 g of a fatty alcohol polyglycol ether and 0.05 ml of 80% acetic acid. The treatment is carried out in a conventional dyeing machine. The bath is then heated in the course of 30 minutes to 80° C., kept for a further 30 minutes at this temperature, and then cooled in the course of 15 minutes to 40° C. The fabric is given an aftertreatment by rinsing it for 30 seconds in running deionised water, then dried at 150° to 170° C. The treated fabric has an excellent white effect.

EXAMPLE 6

5 g of polyacrylonitrile fabric is put at 40° C. into 100 ml of an aqueous bath which contains 0.01 g of the fluorescent whitening agent of the formula (101), 0.1 g of a fatty alcohol polyglycol ether, 0.4 g of 50% sodium chlorite and 0.15 ml of 85% formic acid. The bath is then heated in the course of 30 minutes to 97° C., kept for 30 minutes at this temperature, and then cooled in the course of 15 minutes to 40° C. The above treatment is carried out in a conventional dyeing machine. The fabric is subjected to an aftertreatment by rinsing it for 30 seconds in running deionised water, then dried at 160° C. The treated fabric has a strong white effect.

EXAMPLE 7

5 g of polyamide woven jersey fabric is put at 40° C. into 100 ml of an aqueous bath which contains 0.01 g of the fluorescent whitening agent of the formula (101), 0.3 g of $Na_2S_2O_4.2H_2O$ stabilised with 40% $Na_2P_2O_7$, and 0.1 g of 80% acetic acid. The treatment is carried out in a conventional dyeing machine. The bath is then heated in the course of 30 minutes to 97° C., kept for a further 30 minutes at this temperature, and then cooled in the course of 30 minutes to 40° C. The fabric is given an aftertreatment by rinsing it for 30 seconds in running deionised water, then dried at 180° C. The treated fabric has an excellent white effect.

EXAMPLE 8

A piece of polyamide woven jersey fabric is padded at room temperature with an aqueous liquor which contains, per liter, 0.2 g of the fluorescent whitening agent of the formula (101), 2 g of average to high molecular weight polyphosphates, 15 g of a polyoxyethylene having a molecular weight of about 600, and 5 ml of 80% acetic acid. The pick-up is 110%. The fabric is then thermofixed for 40 seconds at 190° C. The treated fabric has a strong white effect.

EXAMPLE 9

Polyamide fabric is washed for 15 minutes in a liquor of 55° C. which contains 4 g/l of a detergent of the following composition:

| fluorescent whitening agent of the formula (112) | 0.2% |
| alkylarylsulfonate | 15.7% |
| fatty alcohol sulfate | 3.7% |
| coconut fatty acid monoethanolamide | 2.7% |
| sodium tripolyphosphate | 39.0% |
| sodium silicate | 4.0% |
| magnesium silicate | 2.0% |
| carboxymethyl cellulose | 1.0% |
| ethylenediaminetetraacetic acid (sodium salt) | 0.5% |
| sodium sulfate and water to make up 100% | |

The liquor also contains 0.25 g of active chlorine (Javel water). The goods to liquor ratio is 1:20. After it has been rinsed and dried the polyamide fabric has a fine white effect.

EXAMPLE 10

1000 g of polyester granules of the ethylene glycol terephthalate type containing 0.5% of $TiO_2$ (anatase type) are mixed with 0.5 g of a compound of the formula (113) in a Rhönrad mixer. The treated granules are spun in an extruder at 280° C. to a multifilament. The resulting fibres have an excellent white effect of good light fastness.

EXAMPLE 11

A homogeneous mixture of 65 parts of polyvinyl chloride (suspension type), 32 parts of dioctyl phthalate, 3 parts of an epoxidised soyabean oil, 1.5 parts of a stabiliser, 0.5 part of a co-stabiliser, 5 parts of $TiO_2$ (rutile type) and 0.05 part of a compound of the formula (122), is rolled to a sheet at 150° C. on a calender. The resultant sheet has a strong white effect of good light-fastness.

What is claimed is:

1. A v-triazolyl-[4,5-d]-pyrimidine of the formula

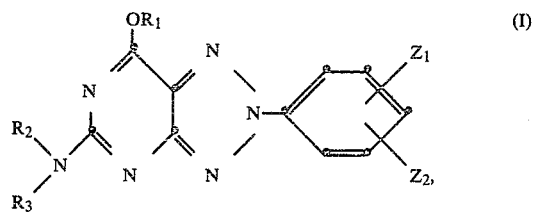

wherein $R_1$ is alkyl of 1 to 12 carbon atoms, alkoxyalkyl containing a total of 3 to 8 carbon atoms, alkenyl of 3 to 6 carbon atoms, phenyl which is unsubstituted or substituted by 1 to 3 members selected from the group consisting of halogen; alkyl or alkoxy each of 1 to 4 carbon atoms, or is a group of the formula

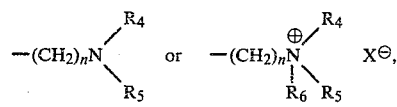

wherein each of $R_4$, $R_5$ and $R_6$ independently is alkyl of 1 to 4 carbon atoms, n is an integer from 2 to 6 and $X^\ominus$ is chloride, bromide, iodide, alkylsulfate, unsubstituted phenylsulfonate or phenylsulfonate ion substituted by halogen, lower alkyl groups or both halogen and lower alkyl groups; $R_2$ is alkyl of 1 to 12 carbon atoms, hydroxyalkyl of 2 to 6 carbon atoms or dialkylaminoalkyl containing 1 to 4 carbon atoms in each alkyl moiety; $R_3$ is hydrogen, alkyl of 1 to 12 carbon atoms or hydroxyalkyl of 2 to 6 carbon atoms, or $R_2$ and $R_3$ together with the nitrogen atom to which they are attached complete a pyrrolidine, piperidine, piperazine or morpholine ring, which can be unsubstituted or substituted by alkyl of 1 to 4 carbon atoms, the piperazine ring being optionally substituted in the 4-position also by hydroxyalkyl of 1 to 4 carbon atoms; $Z_1$ is hydrogen, alkyl of 1 to 6 carbon atoms, alkoxy of 1 to 6 carbon atoms, alkenyloxy of 3 to 6 carbon atoms, hydroxyalkyl of 2 to 4 carbon atoms, alkoxyalkyl containing a total of 3 to 8 carbon atoms, benzyloxy, phenethoxy, halogen, phenoxy, phenoxyalkoxy containing 1 to 3 carbon atoms in the alkyl moiety, or is the group

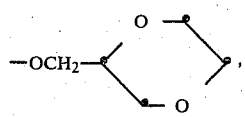

$Z_2$ is hydrogen, alkyl of 1 to 4 carbon atoms, alkoxy of 1 to 4 carbon atoms or halogen, or $Z_1$ and $Z_2$ in the ortho-position to each other together are also the methylenedioxy, ethylenedioxy or methyleneoxymethyleneoxy radical.

2. A v-triazolyl-[4,5-d]-pyrimidine according to claim 1 of the formula

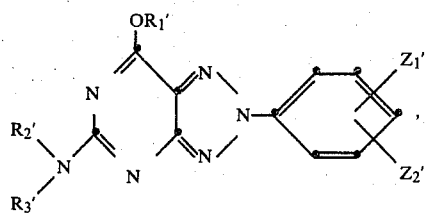

wherein $R_1'$ is alkyl of 1 to 6 carbon atoms, alkoxyalkyl containing a total of 3 to 8 carbon atoms, alkenyl of 3 or 4 carbon atoms, phenyl which is unsubstituted or substituted by one or two members selected from the group consisting of chlorine, fluorine, bromine, or alkyl or alkoxy, each of 1 to 4 carbon atoms, or is a group of the formula

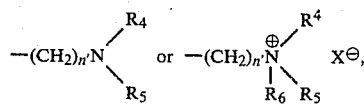

wherein each of $R_4$, $R_5$ and $R_6$ independently is alkyl of 1 to 4 carbon atoms, n' is an integer from 2 to 4 and $X^\ominus$ is chloride, bromide, iodide, alkylsulfate, unsubstituted phenylsulfonate or a phenylsulfonate ion substituted by halogen, lower alkyl groups or both halogen and lower alkyl groups $R_2'$ is alkyl of 1 to 6 carbon atoms or hydroxyalkyl of 2 to 6 carbon atoms; $R_3'$ is hydrogen, alkyl of 1 to 6 carbon atoms or hydroxyalkyl of 2 to 6 carbon atoms, or $R_2'$ and $R_3'$ together with the nitrogen atom to which they are attached complete a pyrrolidine, piperidine, piperazine or morpholine ring, which can be unsubstituted or substituted by alkyl of 1 to 4 carbon atoms, the piperazine ring being optionally substituted in the 4-position also by hydroxy alkyl of 1 to 4 carbon atoms; $Z_1'$ is hydrogen, alkyl of 1 to 4 carbon atoms, alkoxy of 1 to 4 carbon atoms, allyloxy, hydroxyalkoxy of 2 to 4 carbon atoms, alkoxyalkoxy containing a total of 3 to 8 carbon atoms, benzyloxy, phenethoxy, chlorine, bromine, fluorine, phenoxy, phenoxypropoxy, or the group

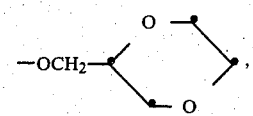

$Z_2'$ is hydrogen, alkyl of 1 to 4 carbon atoms, alkoxy of 1 to 4 carbon atoms, chlorine, bromine or fluorine, or $Z_1'$ and $Z_2'$ together in the ortho-position to each other are also the methylenedioxy, ethylenedioxy or methyleneoxymethyleneoxy radical.

3. A v-triazolyl-[4,5-d]-pyrimidine according to claim 2 of the formula

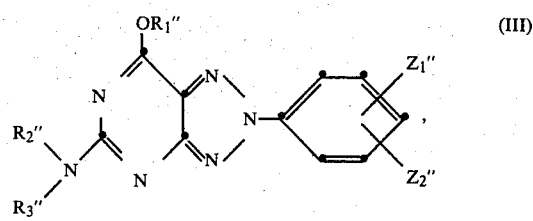

wherein $R_1''$ is alkyl of 1 to 4 carbon atoms, alkoxyalkyl containing a total of 3 to 6 carbon atoms, phenyl, chlorophenyl, methylphenyl, methoxyphenyl, or a group of the formula

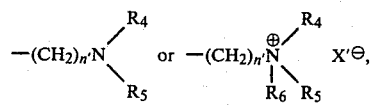

wherein n' is an integer from 2 to 4, each of $R_4$, $R_5$ and $R_6$ independently is alkyl of 1 to 4 carbon atoms and $X'^\ominus$ is a chloride, bromide, iodide or alkylsulfate ion or a phenylsulfonate ion which is unsubstituted or substituted by chlorine, methyl or both chlorine and methyl; $R_2''$ is alkyl of 1 to 4 carbon atoms, $R_3''$ is alkyl of 1 to 4 carbon atoms, or $R_2''$ and $R_3''$ together with the nitrogen atom to which they are attached form the pyrrolidine, piperidine or morpholine ring; $Z_1''$ is hydrogen, alkyl of 1 to 4 carbon atoms, alkoxy of 1 to 4 carbon atoms, allyloxy, hydroxyalkoxy of 2 to 4 carbon atoms, alkoxyalkoxy containing a total of 3 to 6 carbon atoms, benzyloxy, chlorine, or phenoxy; $Z_2''$ is hydrogen, alkyl of 1 to 4 carbon atoms, alkoxy of 1 to 4 carbon atoms or chlorine, or $Z_1''$ and $Z_2''$ together in the 3,4-position are the methylenedioxy, ethylenedioxy or methyleneoxymethyleneoxy radical.

4. A v-triazolyl-[4,5-d]-pyrimidine according to claim 3 of the formula

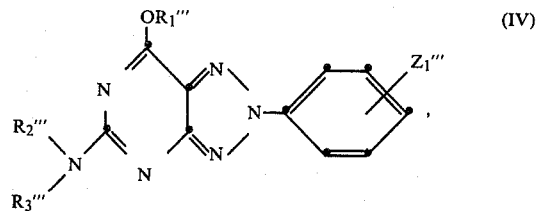

wherein R'''₁ is alkyl of 1 to 4 carbon atoms, alkoxyalkyl containing a total of 3 to 6 carbon atoms, phenyl or a group of the formula

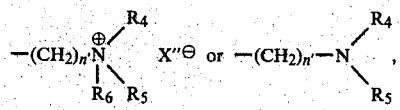

wherein n' is an integer from 2 to 4, each of $R_4$, $R_5$ and $R_6$ independently is alkyl of 1 to 4 carbon atoms, and X'''⊖ is a chloride, bromide, iodide, methylsulfate, ethylsulfate or phenylsulfonate ion; R'''₂ is alkyl of 1 to 4 carbon atoms; R'''₃ is alkyl of 1 to 4 carbon atoms, or R'''₂ and R'''₃ together with the nitrogen atom to which they are attached form the morpholine or piperidine ring; and Z'''₁ is hydrogen, chlorine, alkyl of 1 to 4 carbon atoms, alkoxy of 1 to 4 carbon atoms, allyloxy, hydroxyalkoxy of 2 to 4 carbon atoms, alkoxyalkoxy containing a total of 3 to 6 carbon atoms, or a group of the formula

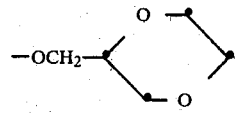

5. A v-triazolyl-[4,5-d]-pyrimidine according to claim 4 of the formula

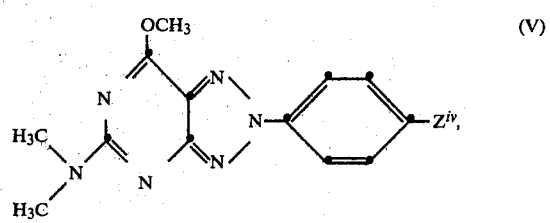

wherein $Z^{iv}$ is alkyl of 1 to 4 carbon atoms, alkoxy of 1 to 4 carbon atoms, hydroxyethyl or methoxyethyl.

* * * * *